United States Patent
Wood (10) Patent No.: US 11,848,106 B1
(45) Date of Patent: Dec. 19, 2023

(54) CLINICAL EVENT OUTCOME SCORING SYSTEM EMPLOYING A SEVERITY OF ILLNESS CLINICAL KEY AND METHOD

(71) Applicant: Michael H. Wood, Detroit, MI (US)

(72) Inventor: Michael H. Wood, Detroit, MI (US)

(*) Notice: Subject to any disclaimer, the term of this patent is extended or adjusted under 35 U.S.C. 154(b) by 264 days.

(21) Appl. No.: 17/215,761

(22) Filed: Mar. 29, 2021

Related U.S. Application Data (60) Provisional application No. 63/001,066, filed on Mar. 27, 2020.

(51) Int. Cl.
- *G16H 50/20* (2018.01)
- *G16H 50/30* (2018.01)
- *G16H 40/20* (2018.01)

(52) U.S. Cl.
CPC .......... *G16H 50/30* (2018.01); *G16H 40/20* (2018.01); *G16H 50/20* (2018.01)

(58) Field of Classification Search
CPC ........ G16H 50/30; G16H 40/20; G16H 50/20; G06F 9/54; G06F 40/30; G06F 40/295; G06F 40/205
USPC ......................................................... 705/2, 3
See application file for complete search history.

(56) References Cited

U.S. PATENT DOCUMENTS

| | | | | |
|---|---|---|---|---|
| 2006/0173663 A1* | 8/2006 | Langheier | ............... | G16H 50/20 703/11 |
| 2012/0016206 A1* | 1/2012 | Ramarajan | ............... | G16Z 99/00 600/300 |
| 2013/0117033 A1* | 5/2013 | Mohlenbrock | ........ | G16H 50/30 705/2 |
| 2015/0112710 A1* | 4/2015 | Haber | .................... | G16H 50/50 705/2 |
| 2015/0213225 A1* | 7/2015 | Amarasingham | ...... | G16H 50/30 705/2 |
| 2018/0268922 A1* | 9/2018 | Greene | .................. | G16H 40/67 |

* cited by examiner

*Primary Examiner* — Mamon Obeid
*Assistant Examiner* — Alaaeldin M Elshaer
(74) *Attorney, Agent, or Firm* — Juneau & Mitchell; Todd L. Juneau (57) ABSTRACT

A clinical event outcome scoring system and method are used to determine a Severity of Illness Clinical Key (SICK) score, which is a probable degree of successful outcome for a patient about to undergo a specific clinical event, such as for example, coronary bypass surgery, hip replacement, bariatric surgery, discharge from a hospital for home recovery, a course of chemotherapy, radiation, or other treatment protocol. The system and method analyzes historical patient data to generate a statistical model for each specific clinical event of interest, which can then be used to determine a SICK score for a patient about to undergo the same clinical event. In some embodiments, the statistical model can be "fine-tuned" to render subcategories of statistical models tailored for certain patient populations about to undergo the same clinical event. In some embodiments, the statistical model can be augmented to take into account "outliers," who have extra challenges not taken into account with the primary statistical model.

2 Claims, 4 Drawing Sheets

CLINICAL EVENT OUTCOME SCORING SYSTEM EMPLOYING A SEVERITY OF ILLNESS CLINICAL KEY AND METHOD

CROSS-REFERENCE TO RELATED APPLICATION

This application claims benefit pursuant to 35 U.S.C. § 119(e) to provisional patent application 63/001,066 filed Mar. 27, 2020, the contents of which are incorporated herein by reference.

TECHNICAL FIELD

This invention pertains to the field of a clinical event outcome scoring system.

BACKGROUND

Severity of illness indexes do not account for the severity of the specific disease processes; they only tabulate a specific risk factor. Therefore, some patients may be much sicker, although they may have the same specific risk factor as another patient. This may be significant when making decisions regarding prescribing a clinical event for a patient, such as surgery, a medical inpatient admission to the hospital, a home care discharge from an inpatient hospital admission or a course of chemotherapy.

One example pertains to the Pay-for-Performance programs. A review of 34 pay-for-performance programs in 14 of the Organisation for Economic Co-operation and Development (OECD) countries (Australia, Canada, Denmark, England, France, Israel, Italy, Japan, Luxembourg, Norway, Republic of Korea, Sweden, Turkey, and the USA), determined that "P4P programs have yet not lived up to expectations." (Health Policy 120(2016): 1125-1140.). Moreover, a Stat News article (Statnews.com; Jan. 30, 2018) describes a number of studies and reports indicating that some programs may actually penalize doctors for caring for the poorest and sickest patients because their "quality scores" suffered. For example, see Annals of Internal Medicine 2/20/18, (The Value-Based Payment Modifier: Program Outcomes and Implications for Disparities) wherein the authors conclude that "Performance differences between practices serving higher- and those serving lower-risk patients were affected considerably by additional adjustments, suggesting a potential for Medicare's pay-for-performance programs to exacerbate health care disparities."

A need remains therefore for a clinical event outcome scoring system that can be used to assess the combination of adverse factors, while integrating the severity level of each factor, impacting a patient. Such a system would be useful in predicting outcomes from a clinical event, e.g., complication rates from surgical procedures, increased length of stay, increased chance of readmission to the hospital after discharge, increased Emergency Department (ED) visits, reoperation, increased utilization of resources (i.e., ICU, CCU), increased need for home health care after discharge from hospital, etc.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

This is a clinical event outcome scoring system and method used to determine a Severity of Illness Clinical Key (SICK) score, which is an analytical tool that can be used in a number of manners to seek to improve the delivery of care to a patient who is going to undergo a clinical event at some point in the future. The system analyzes historical patient data to generate a statistical model for each specific clinical event of interest, which can then be used to determine a SICK score for a patient about to undergo the same clinical event. For example a SICK score can be used to assess the probable degree of successful outcome for a patient about to undergo a specific clinical event, such as coronary bypass surgery, hip replacement, bariatric surgery, discharge from a hospital for home recovery, a course of chemotherapy, radiation, or other treatment protocol and then prescribe a Pre-Clinical Event Care Plan to make adjustments to one or more patient attributes to improve the probable outcome for that patient.

In one embodiment, the statistical model can be "fine-tuned" to render subcategories of statistical models tailored for certain patient populations about to undergo the same clinical event. For example, it could generate one statistical model for high-income people with strong health-insurance and another statistical model for low income people with no health insurance, about to undergo heart bypass surgery. This tuning could help illuminate different patient attributes that may have a greater impact for a patient in one group versus another group, a detail which could be lost in a generic statistical model. In some embodiments, the statistical model can be augmented to take into account "outliers," who have extra challenges not taken into account with the primary statistical model.

Patient attributes comprise: physiological attributes (e.g., clinical data), lifestyle attributes, cultural attributes and optionally other attributes such as genetic attributes, belief attributes, behavior attributes, clinical care attributes, home care attributes etc. They are metrics or indicators of the overall health, cultural, behavioral, psychological, etc. status of a patient. For each clinical event of interest, the system collects and analyzes historical training patient attributes, which include the degree (intensity) of each attribute and the outcomes for each patient who has undergone that clinical event. In one embodiment, the system determines weights for one or more patient attributes by analyzing the proportional contribution of each patient attribute to impacting the outcome of a patient recovering from a specific clinical event in order to generate a statistical model with weighted patient attributes.

Once a statistical model is created pertaining to a clinical event (a Clinical Event Statistical Model), the system collects new patient attribute data and processes it through the statistical model to generate an outcome score for a patient who is considering undergoing the same clinical event at some point in the future. The medical care team of the health care provider can then intervene, prescribe a Pre-Clinical Event Care Plan and help the patient change the value of one or more patient attributes and possibly improve the actual outcome for the patient. Some of the benefits of the information provided by this system and related methods include the ability to provide a tailored, pre-clinical event protocol that could improve the degree of successful outcome for a patient, in addition to providing a means for planning likely hospital resource requirements and/or home health care requirements post-clinical event. It can also be incorporated into a Pay-for-Performance scheme to provide a more accurate description of the quality of care provided.

DETAILED DESCRIPTION

The present invention is a clinical event outcome scoring system and method used to determine a probable outcome score for a patient who is considering undergoing a specific clinical event. A clinical event can refer to any medical procedure, process, and treatment that has an outcome time point. For example, a clinical event could be a coronary bypass surgery, hip replacement surgery, bariatric surgery, discharge from a hospital for home recovery, a course of chemotherapy, a course of radiation, a course of therapy, such as hyperbaric sessions, a course of light therapy, or pharmacologic treatment protocol, which could reasonably be considered to be an "event" with an outcome.

The outcome is assessed using quality performance indicators or metrics used by the medical industry to assess the success of a pharmacologic/technology protocol and/or or procedure.

In one embodiment, the acronym (Severity of Illness Clinical Key) SICK Score is used to indicate the score obtained by using this system and related methods. The score can be conceptualized as an indication for how strong, well or fit a patient's status is prior to undergoing a certain clinical event, as this status relates to the possible outcome/recovery from the clinical event. In general, the stronger a patient's multi-factorial status (health, environment, culture, race, belief, etc.), the stronger they will be to withstand the impact of the clinical event and the faster they will likely recover, relative to cohort patients and assuming that medical treatment is equivalent among the cohort patients. Patient attributes affecting multi-factorial patient status comprise, physiological attributes (e.g., clinical data), lifestyle attributes, cultural attributes, genetic attributes, belief attributes, lifestyle attributes, behavior attributes, clinical care attributes, home care attributes etc.

In one embodiment, the score can be used to assist in determining which patients should be prioritized for a new or existing technology or procedure that is in limited supply, based on patient attributes rather than privilege.

This score provides an analytical tool, which can be used in a number of manners to improve the delivery of care, before and after, to a patient who is going to undergo a clinical event at some point in the future. In general, the faster a patient recovers from a clinical event, the lower the overall costs of the resources required to conduct the event and to support the patient as they recover from the event. For example, the less the number of visits to the emergency department, the less days spent in a hospital bed, etc., the lower the resource costs. Thus, the score also provides an analytical tool which can be used to lower the cost of health care. The score can also be used to improve the precision of Pay-for-Performance schemes as it will provide a realistic "before" and "after" clinical event indicator of each individual patient status.

The score also provides an analytical tool for more precisely categorizing patients with a number of comorbidities, based on historical treatment data, for example, "low risk," "medium risk," and "high risk" of contracting and succumbing to a contagious disease such as COVID-19. For example, it was observed that most patients who died with COVID-19 had a number of comorbidities. This score could provide categories, for example, a "category 5" patient versus a "category 3" patient, could have specific care plans used that have been demonstrated to be most appropriate for the overall status of each category of patient. For example, the objective for a category 2 patient might be to take steps to bolster a still functioning immune system, to assist the body to fight off the virus, vs a different strategy for a category 5 patient, which might include more aggressive pharmacological treatment, combined with high-flow nasal cannula oxygen.

The system generates a statistical model for each type of clinical event (a Clinical Event Statistical Model) using historical patient data ("training patients"). Each Clinical Event Statistical Model is generated from historic patient data by relating a compilation of patient attributes to one or more outcomes (quality performance indicators/metrics) of patients who have undergone the same or similar clinical event. For example, in the case of coronary bypass surgery, the system analyzes the patient attributes of patients who have undergone coronary bypass surgery and relates them to various indices or metrics of outcome for those patients, such as length of stay in the hospital, number of serious complications, return visits to the emergency room department, etc.

In one embodiment, the system is able to calculate a weight for each of the individual patient attributes according to the significance of their relative impact on the outcome of the event. For example, patient attributes such as smoking, hypertension, obesity, age, race, vital signs, etc. would be individually weighted to determine which attributes, if improved, could have the most impact on improving the likely outcome of the event for a patient. Once a statistical model is generated for coronary artery bypass surgery, a new patient can have their attributes inserted into the model and the SICK score calculated, which would be predictive of the outcome if the patient does not change any of their attributes.

In one embodiment, a Pre-Clinical Event Care Plan can be prepared for the patient (analogous to a prescription) detailing how best to improve one or more of the attributes prior to the clinical event (in this example, being surgery). For example, a SICK score can be used to assess the probable degree of successful outcome in preparing a patient for a Clinical Event so that the outcome of the actual future Clinical Event can be improved.

In one embodiment, the system can be used to run a number of "what if" scenarios to develop a Pre-Clinical Event Care Plan with the patient that targets the changes that would have the most significant impact on improving their outcome. For example, it is one thing to look at a patient who is very overweight and state that they should lose some weight prior to surgery. It is another thing altogether to be able to show the patient that if they lose 10 pounds, they would improve the likely success of their outcome by 20 percent, or if they lose 50 pounds, they would improve the likely success of their outcome by 80 percent. Motivation could be provided to the patient by showing them how these precise changes could result in lowering the value of one or more of their patient attributes, could mean the patient will be released from the hospital sooner, have less complications, and less visits to the emergency department, for example. In this type of scenario, the system could be used to motivate and increase patient compliance with a Pre-Clinical Event Care Plan in order to improve the future outcome.

In one embodiment, the system could be used to develop generalized Pre-Clinical Event Care Plans for categories of patients and categories of Clinical Events, by providing information tailored and most relevant to each category of patient. For example, determining whether it is more important to lower hypertension, versus losing weight, or altering some other patient attribute as having the greatest impact on optimizing the potential outcome for a patient. The attributes could include the patient's beliefs about their ability to recover or heal from the clinical event. For example, visualization techniques have been used with chemotherapy to improve the quality of life outcome for patients. In one embodiment, this type of a Pre-Clinical Event Care Plan could be used for patients who are not participating or using the system, but their care team has access to the information generated therein. For example, it might be determined that for a certain category of patients (e.g., high income vs. low income), one general Pre-Clinical Event Care Plan might be more effective for one category and another general Pre-Clinical Event Care Plan might be more effective for another category. For example, this information based on analyzing historic patient data and being updated with current data could be used to determine "best mode" Pre-Clinical Event Care Plans recommended by the Medical Association in a similar manner to how they issue "best mode" treatment plans.

In one embodiment, the system could assist in managing hospital resources, such as planning how many days hospital care will be required before and/or after a clinical event, or likely number of visits to the emergency room might occur post clinical event.

In one embodiment, the system could assist in improving the accuracy and effectiveness of Pay for Performance systems and other systems analyzing the various metrics used in the medical system.

In one embodiment, the system could assist in the development and deployment of new technologies as they become available. It could be used to shorten the learning curve when a new technology/treatment becomes available, because new models can quickly be determined using historical patient data for that new technology in its early stages of development and deployment, as well as continually updated as it is used on new patients. The system could also assist in determining priorities for access to a new technology, such as determining which patients should be prioritized over other patients in the event that there is limited access to the new technology. For example, a new technology might first be deployed with categories of patients for which there is a greater likelihood of success and less risk prior to using it with patients it could harm.

The clinical event outcome scoring system may allow clinical decision support to predict clinical event outcomes in a clinical setting. Additionally, the clinical event outcome scoring system may lead to the development of better clinical event preparation for patients who are predictably poor responders to a clinical event. This can result in a decreased chance of a patient having an untoward event.

The clinical event outcome scoring system may also be used in the context of experimental treatments to recommend an alternative approach that may be advantageous to the patient. The researcher may be able to prescribe a treatment modality that corresponds better, contextually, to a current clinical research initiative.

In one embodiment, this system and its related methods could be applied to athletics, the field of sports medicine and/or performance enhancement, to develop the most efficient training program, the fastest recovery treatments from performance injuries, etc. For example, if a sprinter desires to decrease their 1-minute mile running time by 0.2 sec, the system could be used to determine what would be the most effective elements in a training regimen to develop the athlete's performance abilities in a certain manner. Some examples include a regimen focused on one or more of the following types of activities: e.g., sprinting, slow jogging, jumping exercises, increasing ability to move laterally, weight lifting, focus on repetition, focus on endurance, etc., in addition to psychological enhancement exercises, visualization exercises, etc. In one embodiment, the patient attributes would be the key indicators correlated to the athlete's performance, including physical/physiological attributes, performance attributes, psychological attributes, etc. The outcomes would be the relevant indicators of interest to the athlete (e.g., speed for runner or swimmer, endurance for hockey players, etc.) during a competition. A number of "what if" scenarios could be performed by the system changing the values of the athlete attributes (patient attributes) to determine the greatest likely impact for that cohort of athletes as reflected in the Athletic Performance Statistical Model.

In one embodiment, as with the Clinical Event Statistical Model, the system could conduct analytics on the historical training athlete data and information, to determine which athlete attributes would be the most significant to include in the Athletic Performance Statistical Model.

In one embodiment, the system could be combined with a biofeedback system to enhance the patient attribute data collection and performance outcome data and information.

Patient Attributes

Each patient about to undergo a clinical event can be conceptualized as having a certain overall patient-status, or readiness, strength, etc., to be able to undergo a clinical event and experience a successful outcome, with minimal or no complications and a quick recovery. There are a number of factors, beyond just clinical data that have been shown to impact/influence positively or negatively the outcome of a patient who has undergone a clinical event. These factors can exert positive, negative or neutral impacts on the overall status of the patient with regard to their "preparedness" to undergo a clinical event and could play a role in influencing the outcome of a patient following a clinical event.

For example, it is well known that socioeconomic factors can be an asset or can also place a "burden" on a patient, such as not having access to affordable health care. In some cases, it has been established that a particular race can also exert a negative impact on a patient who is about to undergo a clinical event, such that they will not demonstrate as successful of an outcome as a patient of a different race (*JAMA Surg.* 2019; 154(11):1077). A wide variety of factors are shown or thought to impact the outcome of patients undergoing clinical events such as, health factors (e.g., diabetic), genetic factors (e.g., certain SNPs), cultural factors (strong cultural belief influences), lifestyle factors (smoking, exercise, education), domestic factors (e.g., stable marriage and strong family), home location (e.g., inner city vs suburb), etc.

In this specification, each of these factors are termed patient attributes, the characteristics of which are quantified and/or characterized in a manner that they are able to be classified into levels, indicative of the degree of disease progression or degree of socioeconomic burden.

There are a number of types of patient attributes, which are known to have an impact on patient outcome following a clinical event: physiological attributes, lifestyle attributes, genetic attributes, cultural attributes and belief attributes, for example. Physiological attributes (also referred to as clinical attributes) are indicative of the level or degree of a physiological disorder (sometimes referred to as comorbidities, or risk factors), such as diabetes or hypertension; the more advanced the disorder, the greater the severity of illness of the patient. Physiological patient attributes are clinical data points indicating the degree or level of an abnormality.

Lifestyle patient attributes are socioeconomic, race, age, geographic residence location, income levels, family history of illness, tobacco usage, exercise habits, etc., which have been demonstrated to impact the degree of successful outcome for a patient following a clinical event. For example, with regard to education, "level one education" could be graduate or advanced degree, whereas "level 5 education" could be unable to read or write.

Behavioral attributes include beliefs, such as beliefs about the possibility of recovery; the patient can foresee themselves as the desired outcome of the clinical event (e.g., thinner after bariatric surgery, recovery from a stroke, recovery from a myocardial infarction, being able to walk after a fractured hip repair, etc.).

Genomic attributes include genomics, epigenomics, chromatin state, transcriptomics, proteomics, metabolomics, etc., each of which may be extracted from or at least related to the genome.

Other types of patient attributes include: behavioral attributes (disruptive behavior, bulling, argumentative, confrontational, etc.); psychological attributes (depression, anxiety, bullying, confrontational state, obsessive compulsive, attention deficit disorder, addictive personality, etc.); and intellectual disability attributes. For example, incorporation of a Myers=Briggs type information might demonstrate that certain personality types tend to recover from a clinical event faster than another personality type.

For each clinical event of interest, the system collects and analyzes historical patient attributes. In one embodiment, the system collects the raw data (i.e., lab results such as the actual blood pressure, the blood sugar and the Hbg AIC numbers, race, education level, etc.). For example, the system might collect from patient records, blood pressure readings, HgbA1C readings, the name and dosage of each medication, the BMI, age, gender, serum creatine levels, etc.

In one embodiment, the system will use this clinical data to generate a disease prognosis (e.g., severity of diabetes). In turn, this disease prognosis will be used as the patient attribute, for example, level 1 diabetes, level 3 hypertension, level 3 dyslipidemia, etc. For example, level 3 blood pressure, level 2 blood sugar levels, level 1 HgbA1C, level 3 medication, etc.

For example, with regard to diabetes, five patients could be scheduled to undergo a surgical procedure, wherein diabetes is known to play a role in diminishing the degree of successful outcome from that surgical procedure. Since the severity of the diabetes could vary significantly between these five patients, simply stating that diabetes presents a risk factor, would oversimplify predictable outcomes for any of these patients. What would provide more useful insight would be to also assign a level to the degree or severity of diabetes in a patient, reflecting the severity of the disease process. The severity of diabetes may be indicated by the clinical data collected on the patient (e.g., blood pressure, blood sugar levels, HgbA1C levels, HDL levels, serum creatinine levels, etc.). So, in this example of five patients with diabetes, one could be pre-clinical/early stage diabetes, two could have moderate diabetes and two could have severe diabetes. The severity of the diabetes might play a significant role in influencing the outcome of one type of clinical event, but might not play any role in another type of clinical event.

In one embodiment, the system collects data and information that has already been categorized into levels, degrees, intensities, etc. In one embodiment, the system collects both raw and categorized or partly categorized data and information. In one embodiment, the system converts the raw and/or categorized data and information into a standardized raw data and/or standardized stratified/categorized levels of data and information. For example, the system either collects data and information, which includes the degree (intensity) of each attribute (e.g., level 3 hypertension), or it categorizes the raw data into a category.

Weighting Patient Attributes

In one embodiment, the system analyzes the proportional contribution of each historic training patient attribute (and/or level/degree of each attribute) on impacting the outcome of a patient recovering from a specific clinical event in order to generate a statistical model. The system analyzes the relative impact of each patient attribute on one or more outcome metrics to assign a weight to each attribute. For example, the system could back-calculate the relative impact of each of the attributes on the number of complications, the time required to stay in the hospital, or some other relevant significant outcome metric. In one embodiment, the system analyzes which patient attributes contribute a positive impact on a successful outcome.

For physiological patient attribute data, there are a number of common blood tests, including a complete blood count, blood chemistry tests, blood enzyme tests, blood tests to assess heart disease risk. Blood Glucose Test (diabetes); Calcium Blood Test (kidney disease, bone disease, thyroid disease, intestinal disease, some types of cancer, poor nutrition); Cardiac Enzymes (heart attack); Cholesterol and Lipid Tests (risk of heart disease); C-Reactive Protein Test (infection or inflammation), D-Dimer Test (blood clotting); Erythrocyte Sedimentation Rate Test (inflammation where red blood cells clump together in the body); Folate Test (folate sufficiency); Full Blood Count (infection, anaemia, tiredness or weakness, bleeding or clotting problems, exposure to toxic substances, monitoring response to treatment); HbA1C test (diagnose and monitor diabetes); hCG Test (confirm or monitor pregnancy); International Normalised Ratio Test (blood clotting time); Iron Tests; Kidney Function Tests; Liver Function Tests; Magnesium Blood Tests; Estrogen Blood Test; Testosterone Blood Test; Prostate Specific Antigen Test; Thyroid Function Tests; Vitamin B12 Test; Vitamin D Test.

There are also a number of routine urine tests commonly performed prior to submitting a patient to a clinical event. Thus, other patient attribute data that commonly forms part of patient records results from urinalysis, which is a test of urine and (apart from specialized tests such as pregnancy testing and drug screening) is used to detect and monitor a wide range of disorders, such as urinary tract infections, kidney disease and diabetes. Generally, a urinalysis is conducted as part of a routine medical exam, pregnancy checkup, pre-surgery preparation, or on hospital admission.

A urine sample is evaluated in three ways: visual exam, dipstick test and microscopic exam. Urine is typically clear. Cloudiness or an unusual odor may indicate a problem, such as an infection. Blood in the urine may make it look red or brown. Urine color can be influenced by what a patient has just eaten. A dipstick test checks for: acidity (the pH level indicates the amount of acid in urine—abnormal pH levels may indicate a kidney or urinary tract disorder); concentration (or specific gravity, shows how concentrated particles are in urine—a higher than normal concentration often is a result of not drinking enough fluids); protein (low levels of protein in urine are normal—larger amounts may indicate a kidney problem); sugar) detection of sugar—glucose—on this test usually calls for follow-up testing for diabetes); ketones (could be a sign of diabetes and requires follow-up testing); bilirubin (may indicate liver damage or disease); either nitrites or leukocyte esterase (may be a sign of a urinary tract infection); blood (may be a sign of kidney damage, infection, kidney or bladder stones, kidney or bladder cancer, or blood disorders). A microscopic exam can reveal additional testing may be necessary if above-average levels of the following are observed: white blood cells (leukocytes—may be a sign of an infection); red blood cells (erythrocytes—may be a sign of kidney disease, a blood disorder or another underlying medical condition, such as bladder cancer); bacteria or yeast cells (may indicate an infection); casts (tube-shaped proteins—may form as a result of kidney disorders); and crystals (may be a sign of kidney stones).

Grading Scale—Patient Attributes

A grading scale is used to indicate the level of a patient attribute that is known and/or suspected of influencing a patient's outcome/recovery from a specific clinical event. In one embodiment, the system will use clinical data as the patient attributes. For example, level 3 blood pressure, level 2 blood sugar levels, level 1 HgbA1C, level 3 medication, etc. In one embodiment, the system will use the clinical data to generate a disease prognosis (e.g., severity of diabetes) and use the disease as the patient attribute (e.g., diabetes, hypertension, dyslipidemia, etc.)). In turn, this disease prognosis will be used as the patient attribute, for example, level 1 diabetes, level 3 hypertension, level 3 dyslipidemia, etc.

In one embodiment, a two-grade severity scale (low, high) is used to indicate the severity level of a patient attribute. In this embodiment, zero would be used to indicate the attribute is in the normal range and therefore would not negatively impact the patient's outcome from a clinical event. Attributes would be assigned either a low or high level, thereby greatly simplifying the categorization of patient attributes into levels.

In one embodiment, a three-grade scale (low, medium, high) is used to indicate the degree of a patient attribute. In this embodiment, zero would be used to indicate the attribute is in the normal range and therefore would not negatively impact the patient's outcome from a clinical event. Attributes would be assigned either a low, medium or high level, thereby simplifying the categorization of patient attributes into levels.

In one embodiment, a four-grade scale is used to indicate the degree of a patient attribute. Thus, zero would be used to indicate an absence of the attribute, one would be used to indicate the minimal measurable attribute, and four would be used to indicate the highest extreme of this attribute level. A level of two would be assigned to indicate a slightly advanced stage of this attribute and a level of four would be assigned to indicate a very advanced stage/degree of this attribute Clinical Events For the purposes of this system and its related methods, specific clinical events can include different types of surgery, admission to hospital, a course of treatment (e.g., radiation, chemotherapy), the need for home health care post discharge from the hospital, Emergency Department (ED) visits, the need for physical therapy or the need for occupational therapy.

Surgeries can be categorized into inpatient surgery, wherein the patient is admitted to a hospital, and ambulatory surgery (AS) or outpatient surgery, which is a planned operation where the patient is not expected to be admitted to a hospital. Because of the draw upon hospital resources, the SICK scoring system is generally designed for inpatient clinical events, though it can also be applied to predict possible outcomes from AS clinical events.

In one embodiment, inpatient invasive surgical procedures can be classified by the body system of interest. When a surgical procedure is performed on one organ system or structure, it may be classed by the organ, the organ system or tissue involved. Examples include cardiac surgery (performed on the heart), gastrointestinal surgery (performed within the digestive tract and its accessory organs), and orthopedic surgery (performed on bones or muscles).

Other classification examples include: cardiovascular, respiratory, urinary, hematologic, lymphatic, female genital, digestive, nervous, musculoskeletal, skin, endocrine, male genital, ear nose mouth and pharynx systems. The majority of eye, ear, nose/mouth/pharynx are performed in an AS setting, whereas the majority of cardiovascular, respiratory, and urinary systems are performed in the inpatient setting.

Each of these systems can be further classified into types of surgery. For example, cardiovascular surgeries can be classified into: coronary artery bypass grafting (CABG) (surgical procedure used in which the blocked portion of the coronary artery is bypassed with another piece of blood vessel) is the most common type of heart surgery, used to treat patients who have severe coronary heart disease (CAD). Other common types of heart surgery include: aortic surgery (surgery to repair or replace aortic aneurysms and aortic dissections); aortic valve surgery (surgery to repair or replace an aortic valve that is not working correctly); arrhythmia surgery (surgical procedure to correct irregular heart rhythms such as atrial fibrillation or ventricular tachycardia); congenital heart surgery (corrective surgery to fix or treat a genetic heart defect); heart transplant (a surgical option to treat advanced heart failure, a condition that occurs when the heart can't pump enough oxygenated blood to meet the needs of the body's organs); left ventricular assist device (LVAD) (a mechanical device which aids in the pumping function of the blood); left ventricular remodeling/ surgical ventricular restoration; (a technique that provides the heart with a more normal shape after a heart attack, allowing it to pump blood more efficiently); myectomy/ myotomy (a surgical treatment option that removes a portion of the enlarged heart wall); trans myocardial revascularization (TMR) (a procedure used to relieve severe angina or chest pain in patients who aren't candidates for bypass surgery or angioplasty); and valvular surgery (heart valve surgery used to repair or replace diseased heart valves).

In one embodiment, clinical events can be classified according to the types of events measured in various national hospital surveys. For example, the following are statistics on the frequency of inpatient surgery procedures for 2010. Data is from the National Hospital Discharge Survey 2010: arteriography and angiocardiography—2.4 million procedures; caesarean section 1.3 million procedures; diagnostic ultrasound—1.1 million procedures; endoscopy of small intestine—1.1 million procedures; cardiac catheterizations—1 million procedures; total knee replacement—719,000 procedures; reduction of fracture—671,000 procedures; balloon angioplasty of coronary artery or coronary atherectomy—500,00 procedures; endoscopy of large intestine—499,000 procedures; hysterectomy—498,000 procedures; insertion of coronary artery stent—454,000 procedures; coronary artery bypass graft—395,000 procedures; and total hip replacement—332,000 procedures.

In one embodiment the SICK scoring system generates statistical models for each of the most common clinical events. For example, the SICK scoring system generates one statistical model for caesarean section surgical procedures, another one for total knee replacement, another one for hysterectomy, another one for total hip replacement, another one for bariatric surgery, etc.

In one embodiment, the SICK scoring system generates a statistical model for a number of clinical procedures where the involvement of the patient attributes and their impact on clinical event outcomes are very similar. For example, the SICK scoring system generates one statistical model for many surgical procedures requiring general anaesthesia, such as total knee replacement, total hip replacement, coronary artery bypass, etc.

Clinical Event Outcomes

Outcomes from a clinical event comprise the indices, metrics, and/or quality performance indicators that express the degree to which a patient has successfully or unsuccessfully recovered from the event, relative to the historical data of other clinical event cohorts. The indicia could be: days of recovery time required in the hospital, the number of minor complications, the number of major complications, etc., ranging up to death. If the clinical event is a course of radiation, the medical records of a patient would include the key indicators of performance and recovery, such as a fragility index, patient complaints, In general, each type of clinical event will have what is considered to be a typical recovery time/results, performance indicators, etc. based on historical data.

In one embodiment, each type of clinical event will have a historical profile of adverse events (e.g., complications), which can be categorized into levels or grades, for example: low (Grade I), medium (Grade II) and high (Grade III). For example, a patient recovering from coronary artery bypass surgery, could be characterized as having a Grade I outcome if they fall at the low end of the spectrum of issues, complications, extended time required in and/or out of the hospital to recover, etc. Alternatively, a patient recovering from coronary artery bypass surgery could be characterized as having a Grade III, or higher if they die as a result of issues with the surgery.

In one embodiment, the outcome could be considered to be the summation of graded adverse events. In another embodiment, the outcome could be considered to be the weighted summation of graded adverse events. In one embodiment, the outcome could be evaluated for one specific factor such as for example, recovery days required in hospital, or number of non-life-threatening complications.

Grading Scale—Clinical Event Outcomes

A grading scale is used to indicate the severity or degree of patient outcomes from a specific clinical event. In one embodiment, the system will use the summation of weighted individual outcome indicia, such as recovery days in the hospital, visits to an emergency room, serious complications, etc., to determine an outcome score. In one embodiment, the system will use the outcome indicia to generate a compilation for each level out outcome score, such as for example, level 4 means 4 days of hospital recovery time (when 2 days is normal recovery time), plus 3 major complications, plus the requirement for re-surgery, etc.)

In one embodiment a five-grade scale is used to indicate the degree of a condition/attribute. Thus, zero would be used to indicate an absence of the attribute, one would be used to indicate the minimal measurable attribute, and five would be used to indicate the highest extreme of this attribute. A level of three would be used to indicate a midway point between the level five. A level two would be used to indicate a midway point between level one and level three, and a level four would be used to indicate a midway point between level three and level five.

In one embodiment, the method of developing a clinical event statistical model for a particular clinical event entails using a grading scale to categorize the outcomes (summation of adverse events) observed for a population of patients who have gone through the same clinical event.

For example, in one embodiment, levels such as 1-10 can be assigned to categories of patient outcomes, such as:

Level 1: the ideal patient outcome for that clinical event;
Level 2: increased hospital recovery time;
Level 3: increased hospital recovery time+2 low grade (Grade I) complications;
Level 4: increased hospital recovery time+>2 low grade (Grade I) complications+1 medium (Grade II) complication
Level 5: increased hospital recovery time+4 low grade (Grade I) complications+>2 medium (Grade II) complications
Level 6: increased hospital recovery time+>4 low grade (Grade I) complications+>4 medium (Grade II) complications+1 high (Grade III) complications
Etc. . . . .
Level 10: death within 30 days.

In this embodiment, the training module would generate a clinical event statistical model, which would output a number ranging from 1-10, or some variation thereof such as 0.1-1. In one embodiment, a low, medium, high grading scale is used to evaluate the outcome indicia. For example, Grade I could be non-life-threatening complications; Grade II could be potentially life-threatening complications and Grade III could be life-threatening complications associated with residual and lasting disability. The patient historical data would indicate which types of outcome indicia would fall within each Grade. For example, surgical site infection might be considered a Grade I complication, whereas a wound infection requiring reoperation could be considered a Grade II complication and cardiac arrest could be considered a Grade III complication.

For example, if the system is evaluating low grade complications, 0% to 4% rate; >4% to ≤6%; and >6% could be used to rate low, medium and high numbers of patients presenting low grade complications following a clinical event such as surgery. The serious complication rate could be, for example: 0% to ≤2.4%; >2.4% to ≤2.7%; and >2.7% to indicate low, medium and high numbers of patients presenting serious complications following a clinical event such as surgery.

Data Sets of Patient Attributes and Outcomes

For simplicity, throughout this discussion, patients having data used as training data to generate a SICK Score Statistical Model may be referred to herein as "training patients"

and patients, who are about to undergo a clinical event, having data that is applied to the statistical model to predict SICK Scores may be referred to herein as "current patients." However, this is for ease of discussion only. Data from "current patients" may be added to the training data and the training data may be continuously or periodically updated to keep the statistical model up to date. Additionally, training patients may also have data applied to the statistical model to predict additional patient attributes.

The list of patient attributes chosen for generating a statistical model needs to be sufficiently comprehensive to reflect the status of the major systems of the patient's body in addition to the life context of the patient, but sufficiently concise such that the medical personnel can obtain the detailed information for each patient (e.g., information from blood and urine tests, physical examination, patient questionnaire). For example, it would not be practical to include MRI results within this list of attributes, unless this is a procedure that is almost always done prior to a certain clinical event. Moreover, the information should be in existing patient records, such that the system can easily populate its database.

One skilled in the art would know of a number of methods and techniques known in the art for obtaining (historical) training data from existing patient files and or databases relevant to a particular clinical event of interest. For example, in a study published in Ann. Surg (2014 April 259(4):577-681), the authors describe how they populated a data set in order to evaluate whether existing pay-for-performance schemes improve surgical outcomes. They describe how in order to generate a robust data set reflecting diversity among patients, they chose data from 12 states (Arizona, California, Florida, Iowa, Massachusetts, Maryland, North Carolina, Nebraska, New Jersey, New York, Washington and Wisconsin), choosing these because they (1) were geographically dispersed across the United States, (2) were available for the period they were studying, and (3) had relatively large sample sizes. They obtained data (time period 2003-2009) from the State Inpatient Database (SID) of each of these states. This data set is maintained and distributed as part of the Healthcare Cost and Utilization Project of the Agency for Healthcare Research and Quality, and contains all inpatient discharges from short-term, acute-care, non-federal, general, and other specialty hospitals in participating states. The discharge records from these databases contain information collected as part of billing records, including patient demographics, *International Classification of Diseases, Ninth Revision, Clinical Modification* (ICD-9-CM) procedures, diagnoses, expected payer, admission and discharge dates, and disposition. Data on hospital characteristic was obtained from the American Hospital Association Annual Survey. The investigators were able to identify the patients who had undergone a specific clinical event by using appropriate ICD-9-CM procedure codes. For example, they studied coronary artery bypass surgery (36.10-19), hip replacement (81.51-52), and total knee replacement (81.54), excluding patients with procedure codes indicating that other operations were simultaneously performed.

The Severity Illness Clinical Key (SICK) Score Statistical Model

One skilled in the art would appreciate that there are a number of ways to conceptualize a SICK Score statistical model (Clinical Event Statistical Model) generated for each type of clinical event. In one embodiment, a statistical model is generated for a singular clinical event, such as a specific type of surgery (for example, coronary bypass surgery, bariatric surgery, knee replacement surgery, etc.). In one embodiment, a statistical model is generated for a group of specific clinical events where the system determines from the historical training patient data that the processes are sufficiently similar to use the same statistical model, for example a category for major surgery (Major Surgery Statistical Model) vs. a statistical model for minor surgery (Minor Surgery Statistical Model).

In one embodiment a statistical model generated for a clinical event is generically termed a Clinical Event Statistical Model. In one embodiment, a statistical model generated for a clinical event is specifically referred to using the name of the clinical event in combination with Statistical Model. For example, the Major Surgery Statistical Model, the Chemotherapy Statistical Model, the Coronary Artery Bypass Statistical Model, The Caesarian Section Statistical Model, etc.

In one embodiment, a Clinical Event Statistical Model can be described by:

$$wf\alpha(att\ x)+wf\beta(att\ x)+wf\chi(att\ x)+wf\delta(att\ x)+wf\varepsilon(att\ x)+\text{etc.}\ldots=\text{outcome}$$

where:
  wf=weighting factor; values represented by $\alpha$, $\beta$, $\chi$, $\delta$, $\varepsilon$, $\phi$, $\gamma$, $\eta$, $\iota$, etc.
  att=attribute (identity)+level (x), wherein
    In one embodiment, x can vary between 0-3 (e.g., normal, low, medium, high); or
    In one embodiment, x varies from 0-5; or
    In one embodiment, x can vary between 0-4; or
    In one embodiment, x can vary between 0-10
  Or: $\alpha$ (att x)+$\beta$ (att x)+$\chi$ (att x)+$\delta$ (att x)+$\varepsilon$ (att x)+ etc. . . . =outcome
    For example: $\alpha$ (hypertension 3)+$\beta$ (diabetes 2)+$\chi$ (race 5)+ . . . =outcome One skilled in the art would appreciate that there are a number of ways to convert the historic training patient outcome information into graded levels, some of which are described earlier under the section titled, "Grading Scale—Clinical Event Outcomes", depending upon how one wants to quantify outcomes, which would be relevant to the objectives of the system. Once the outcome information has been converted into graded levels, the system will be able to back-calculate the weighting factors for each leveled patient attribute (wf=weighting factor; values represented by $\alpha$, $\beta$, $\chi$, $\delta$, $\varepsilon$, $\phi$, $\gamma$, $\eta$, $\iota$, etc.), by analyzing thousands of patient records for patients having undergone the same clinical event, to generate a clinical event statistical model.

For example, a statistical model for a specific clinical event could conceptually look like:

$$0.8(\text{hypertension }x)+0.5(\text{diabetes }x)+0.1(\text{race }x)+\text{etc.}\ldots=\text{SICK Score}$$

Determining the Outcome Side of the Equation

In order to generate a Clinical Event Statistical Model, the training module of the system imports historical training patient data for both the patient attributes and their outcomes following a specific type of clinical event. For example, if the clinical event is a round of chemotherapy or radiation therapy, the patient attributes could include the type, stage and location of a cancer in addition to the other patient attributes and the outcomes could include Pay-for-Performance indicators, fragility index scores, tests or scans indicating that a tumor has responded to the radiation, relief of symptoms, patient complaints, nausea, vomiting, etc. If the system is generating a Clinical Event Statistical Model for a hip replacement surgery, the outcomes can include factors such as: post-operative days in hospital, number of minor complications, number of major complications, number of out-patient visits to emergency department, etc.

Ways to Convert Outcome Information into Numerical Information

In one embodiment, the outcome side of the equation uses the outcome factors and calculations that the pay-for-performance schemes use to grade performance. In one embodiment, the system uses historical Pay-for-Performance outcome data, filtering out the points not pertaining directly to the patient outcomes. In one embodiment, the system can be used to validate existing Pay-for-Performance systems.

In other embodiments, outcome (historical) can be determined in different manners In one embodiment, the system would use one specific outcome event to back-calculate weighting factors for the summation of patient attribute formula relative to that one outcome, such as days in hospital, or number of major complications. In this embodiment the system would generate a statistical model for each outcome of interest following a specific clinical event.

The Design of the System and Method

Figure 1:
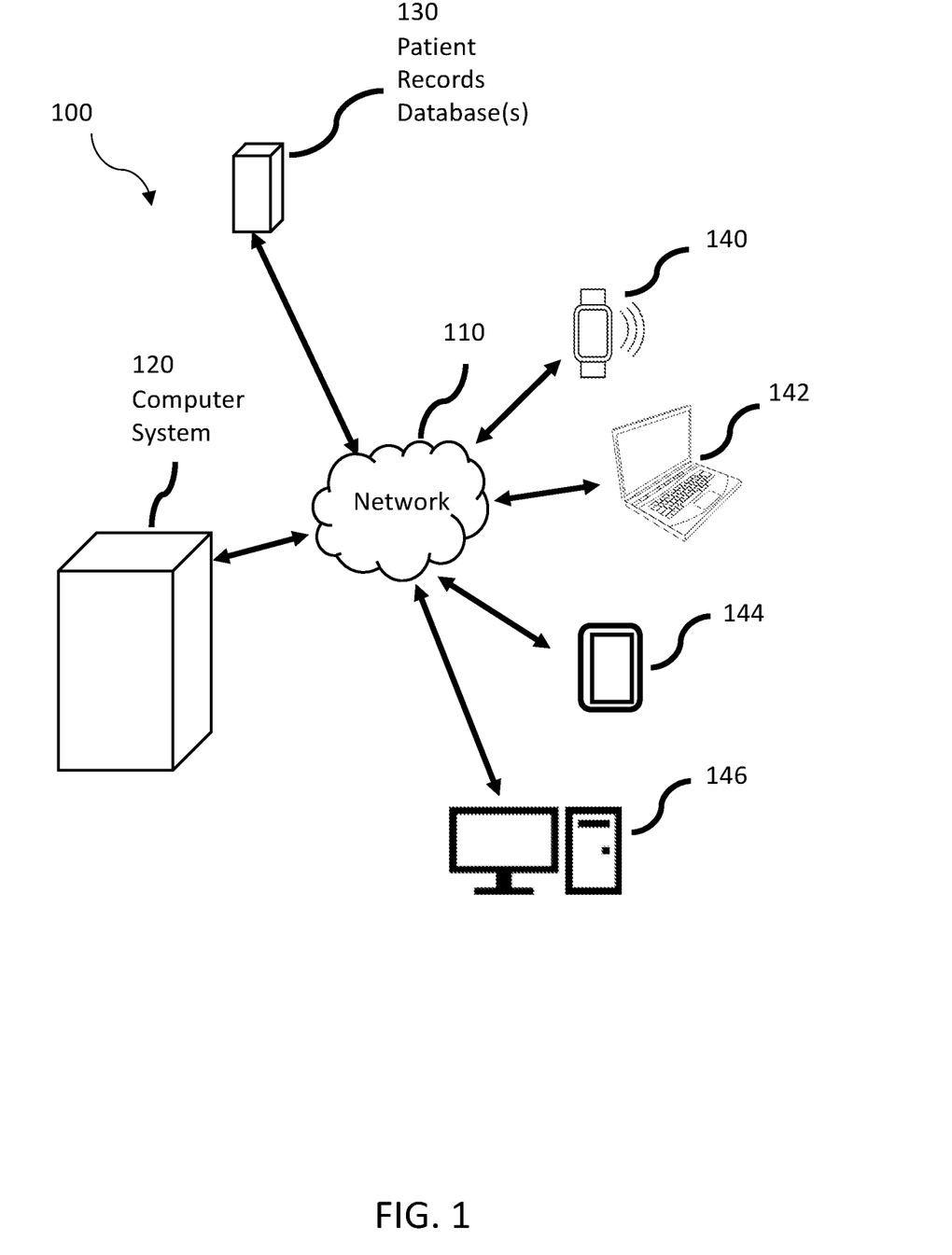
FIG. 1 is a simplified block diagram of an exemplary embodiment of a clinical predictive and monitoring system and method according to the present disclosure.

Referring to FIG. 1, a simplified block diagram of an exemplary embodiment of a clinical event outcome scoring system 100 and method according to the present disclosure using various machine learning techniques to generate a statistical model for a clinical event, which is then used to calculate a SICK score for patients about to undergo a similar clinical event, by inputting the patient's clinical and non-clinical patient attributes into the system.

The clinical event outcome scoring system 100 and method includes a patient computer system 120 and a plurality of client devices 140, 142, 144, 146 which may be communicatively connected through a network 110, as described below. In one embodiment, the computer system 120 and the client devices may communicate via wireless signals over a communication network 110, which can be any suitable local or wide area network(s) including a WiFi network, a Bluetooth network, a cellular network such as 3G, 4G, Long-Term Evolution (LTE), 5G, the Internet, etc. In some instances, the client devices 140, 142, 144, 146 may communicate with the communication network 110 via an intervening wireless or wired device, which may be a wireless router, a wireless repeater, a base transceiver station of a mobile telephony provider, etc.

The client devices may include, by way of example, a tablet computer, a smart watch 140, a network-enabled cell phone 144, a wearable computing device, a personal digital assistant (PDA), a mobile device smart-phone also referred to herein as a "mobile device," a laptop computer 142, a desktop computer 146, wearable biosensors, a phablet, any device configured for wired or wireless RF (Radio Frequency) communication, etc. Moreover, any other suitable client device that records patient attribute data, clinical data, demographic data, polypharmacy data, for patients may also communicate with the clinical assessment scoring system 100.

In some embodiments, the patient may enter data into the desktop computer 146 for example, such as answers in response to a patient survey including questions regarding the patient's demographics, medical history, socioeconomic status, exercise patterns, law enforcement history, sleep cycle, circadian rhythm, etc. In other embodiments, the health care provider may enter the data.

Each of the client devices 140, 142, 144, 146 may interact with the clinical event outcome scoring system to transmit the patient attribute data for a patient. In some embodiments, patient attribute data may be collected periodically (e.g., every month, every three months, every six months, etc.) to identify changes to the patient's SICK score over time (e.g., from unemployed to employed, single to married, etc.). Also, in some embodiments, at least some of the patient attribute data may be recorded by a health care provider via the health care provider's client device or may be self-reported via the patient's client device.

Generating a Statistical Model for a Clinical Event

The clinical event outcome scoring system 100 and method includes a computer system 120 adapted to receive a variety of clinical and non-clinical training data relating to patients ("training patients") who have undergone a clinical event, which is used to determine a statistical model for that clinical event. The computer system 120 may comprise a number of computing devices, including servers, that may be located locally or in a cloud computing farm. The computer system 120 may comprise one or more local or remote computer servers operable to transmit data and communicate via wired and wireless communication links and computer networks. If the design of the computer system 120 is such that the data store is separate, the data paths between the computer system 120 and the data store may be encrypted or otherwise protected with security measures or transport protocols now known or later developed.

Figure 2:
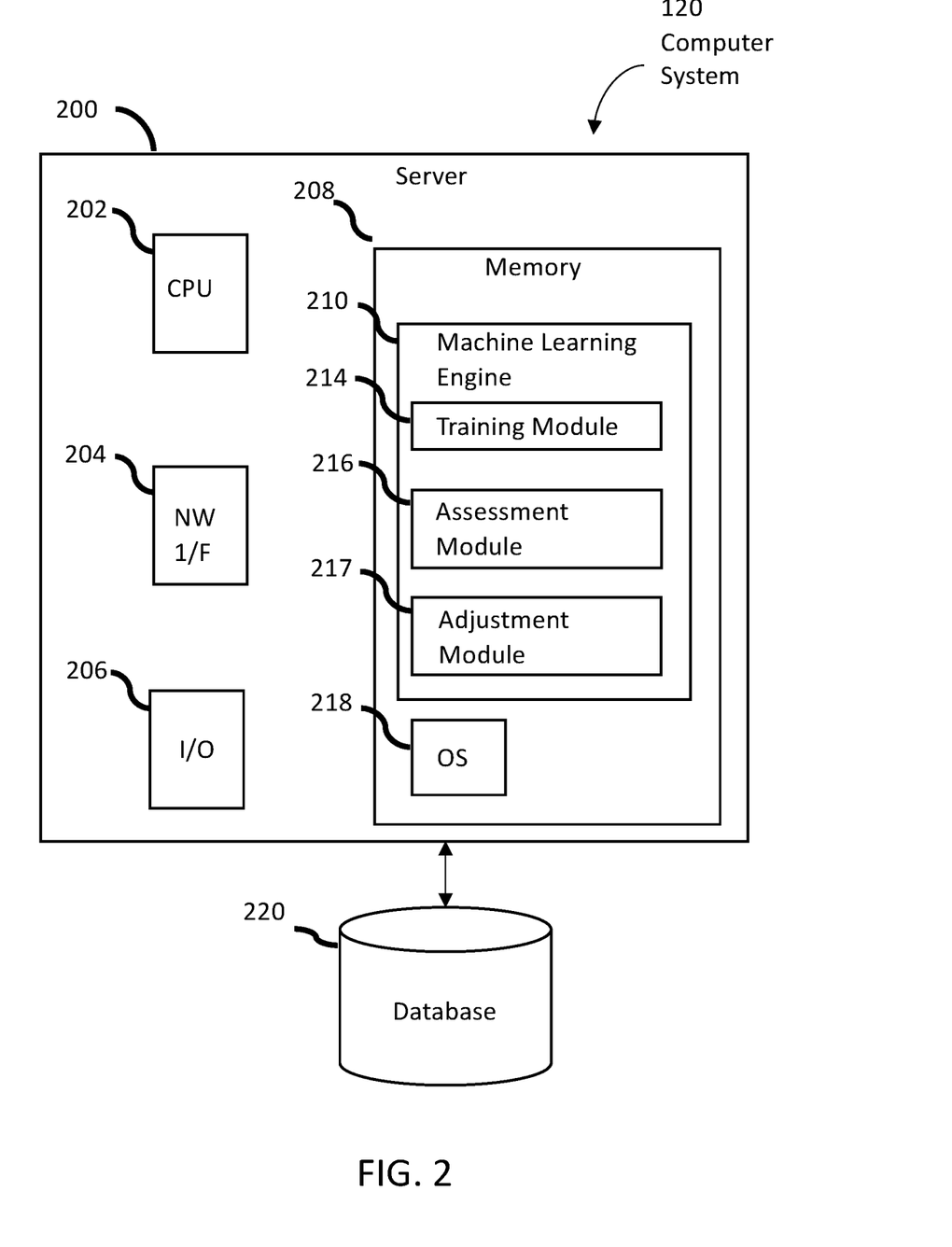
FIG. 2 is a simplified block diagram of an exemplary embodiment of a computer system according to the present disclosure.

The computing system 120 comprises one or more servers 200, wherein in one embodiment, as shown in FIG. 2, the server 200 may be a cloud based server, an application server, a web server, etc., and includes a memory 208, one or more processors (CPU) 202 such as a microprocessor coupled to the memory 208, a network interface unit 144, and an 110 module 206 which may be a keyboard or a touchscreen, for example. In one embodiment, the clinical event outcome scoring system 100 and method is a "stand-alone" service, such as a SaaS service. In one embodiment, the clinical event outcome scoring system 100 and method is incorporated into a health information management system that, for example, combines practice management, electronic health record system, and care coordination.

The data received by the clinical event outcome scoring system 100 and method may include electronic medical records (EMR) that include both clinical and non-clinical data. The EMR data may be received from entities such as hospitals, clinics, pharmacies, laboratories, and health information exchanges, including: vital signs and other physiological data; data associated with comprehensive or focused history and physical exams by a physician, nurse, or allied health professional; medical history, prior allergy and adverse medical reactions; family medical history; prior surgical history; emergency room records, medication administration records; culture results; dictated clinical notes and records; gynecological and obstetric history; mental status examination; vaccination records; radiological imaging exams; invasive visualization procedures; psychiatric treatment history; prior histological specimens; laboratory data; genetic information; physician's notes; networked devices and monitors (such as blood pressure devices and glucose meters); pharmaceutical and supplement intake information; and focused genotype testing.

The EMR non-clinical data may include, for example, social, behavioral, lifestyle, and economic data; type and nature of employment; job history; medical insurance information; hospital utilization patterns; exercise information; addictive substance use; occupational chemical exposure; frequency of physician or health system contact; location and frequency of habitation changes; predictive screening health questionnaires such as the patient health questionnaire (PHQ); personality tests; census and demographic data; neighborhood environments; diet; gender; marital status; education; proximity and number of family or caregiving assistants; address; housing status; social media data; and educational level. The non-clinical patient data may further include data entered by the patients, such as data entered or uploaded to a social media website.

Additional sources or devices of EMR data may provide, for example, lab results, medication assignments and changes, EKG results, radiology notes, daily weight readings, and daily blood sugar testing results. These data sources may be from different areas of the hospital, clinics, patient care facilities, patient home monitoring devices, among other available clinical or healthcare sources.

The clinical event outcome scoring system 100 and method may further receive data from data bases 130 of health information exchanges (HIE). HIEs are organizations that mobilize healthcare information electronically across organizations within a region, community or hospital system. HIEs are increasingly developed to share clinical and non-clinical patient data between healthcare entities within cities, states, regions, or within umbrella health systems. Data may arise from numerous sources such as hospitals, clinics, consumers, payers, physicians, labs, outpatient pharmacies, ambulatory centers, nursing homes, and state or public health agencies.

The system 100 and method is further adapted to receive user preference and system configuration data from clinicians' computing devices (mobile devices, tablet computers, laptop computers 142, desktop computers 146, servers, etc.) in a wired or wireless manner. These computing devices are equipped to display a system dashboard and/or another graphical user interface to present system data and reports. The graphical user interfaces are further adapted to receive the user's (healthcare personnel) input of preferences and configurations, etc. The data may be transmitted, presented, and displayed to the clinician/user in the form of web pages, web-based message, text files, video messages, multimedia messages, text messages, e-mail messages, and in a variety of suitable ways and formats.

As shown in FIG. 1, the clinical event outcome scoring system 100 and method may receive data streamed real-time, or from historic or batched data from various data sources. Further, the system 100 and method may store the received data in a data store or process the data without storing it first. The real-time and stored data may be in a wide variety of formats according to a variety of protocols, including CCD, XDS, HL7, SSO, HTTPS, EDI, CSV, etc. The data may be encrypted or otherwise secured in a suitable manner. The data may be pulled (polled) by the system 100 and method from the various data sources or the data may be pushed to the system 100 and method by the data sources. Alternatively, or in addition, the data may be received in batch processing according to a predetermined schedule or on-demand. The data store may include one or more local servers, memory, drives, and other suitable storage devices. Alternatively, or in addition, the data may be stored in a data center in the cloud.

The memory may be tangible, non-transitory memory and may include any types of suitable memory modules, including random access memory (RAM), read only memory (ROM), flash memory, other types of persistent memory, etc.

The clinical event outcome scoring system server 200 is described in more detail below with reference to FIG. 2. The memory may store, for example instructions executable on the processors for an operating system (OS) 218 which may be any type of suitable operating system 218 such as modern smartphone operating systems, for example. The memory may also store, for example, instructions executable on the processors for a machine learning engine, which may include a training module 214 to generate a statistical model for a clinical event, a SICK score assessment module 216 for calculating the SICK score of a current patient about to undergo a clinically related clinical event and an adjustment module 217 configured to adjust parameters in the statistical model in response to trends in the patient data. In some embodiments, the machine learning engine may be a part of one or more of the client devices, the system 100 server 200, or a combination of the server 200 and the client devices.

The machine learning engine 210 may obtain a set of training data by receiving physiologic and lifestyle patient attribute data from the training patients, including the outcomes observed for a cohort of patients having undergone the same clinical event. The training module 214 may then analyze the patient attribute data to generate a statistical model for each category of clinical event. For example, a first statistical model may be generated for determining a likelihood that a current patient will experience problems following heart surgery, a second statistical model may be generated for determining a risk of poor outcomes following a series of chemotherapy treatments, a third statistical model may be generated for determining a risk of suffering from a blood clot following an inpatient hospital admission, a fourth statistical model may be generated for determining a likelihood of a negative response to a series of radiation treatments. In some embodiments, each statistical model may be combined in any suitable manner to generate an overall statistical model for predicting patient responses to clinical events.

In any event, the set of training data may be analyzed using various machine learning techniques, including, but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based spatial clustering of applications with noise, ordering points to identify the clustering structure, etc.), association rule learning algorithms (e.g., apriori algorithm, Eclat algorithm, etc.), Bayesian algorithms (e.g., naive Bayes, Gaussian naive Bayes, multinomial naive Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked autoencoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc.

In a testing phase, the training module 214 may compare test patient attribute data for a test patient to the statistical model to determine a likelihood of a specific adverse outcome event.

If the training module 214 makes the correct determination more frequently than a predetermined threshold amount, the statistical model may be adjusted to reflect a tighter correlation. On the other hand, if the training module does not make the correct determination more frequently than the predetermined threshold amount, the training module may continue to obtain training data for further training.

Figure 3:
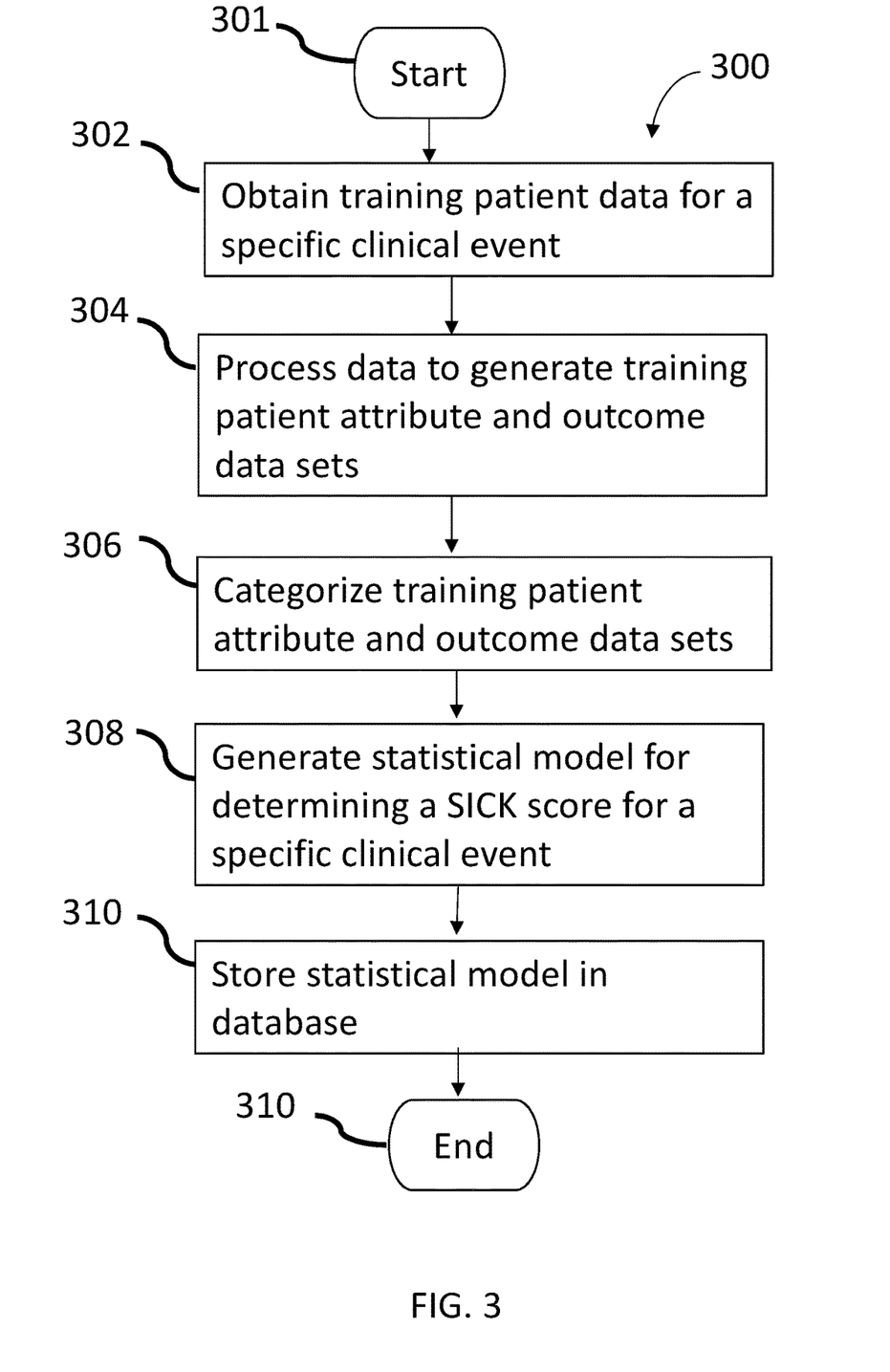
FIG. 3 is a simplified flowchart of an exemplary embodiment of a clinical predictive and monitoring method for generating a statistical model according to the present disclosure.

FIG. 3 is a simplified flowchart of one exemplary embodiment of a clinical event outcome scoring system and method 100 for generating a statistical model for a specific clinical event according to the present disclosure. Because the system 100 receives and extracts data from many disparate sources in myriad formats pursuant to different protocols, the incoming data must first undergo a multi-step process before they may be properly analyzed and utilized. The computer system 120 of the clinical event outcome scoring system 100 and method includes a data integration logic process that further includes a data extraction process, a data cleansing process, and a data categorization process. These processes may be performed in parallel, iteratively, and interactively.

The data extraction process extracts clinical and non-clinical data from data sources in real-time or in batches either directly or through the Internet, using various technologies and protocols. Preferably in real-time, the data cleansing process "cleans" or pre-processes the data, putting structured data in a standardized format and preparing unstructured text for natural language processing (NLP) to be performed in the data categorization process. The system may also receive "clean" data and convert them into desired formats (e.g., text date field converted to numeric for calculation purposes).

This data categorization process converts the raw patient data into categories or levels. In one embodiment, the data categorization process analyzes the representation of a particular data feed against a meta-data dictionary. In embodiments where the level of a disease such as diabetes is used, rather than the clinical data, the meta-data dictionary would be used to convert the clinical data into a stage of disease. The same process would apply for generating levels for the clinical outcomes. A committee would likely determine how the levels of disease would be categorized in addition to the levels out clinical event outcomes are determined. This information would be stored in the meta-data dictionary.

The statistical model generating process is operable to generate an appropriate statistical model for a type of clinical event using the historical data of historical patients who have undergone that type of clinical event, which can then be used to calculate a SICK score for a patient who is planned to undergo the same type of clinical event. The statistical model generating process includes a de-identification/re-identification process that is adapted to remove all protected health information according to HIPAA standards before the data is transmitted over the Internet. In one embodiment, it is also adapted to re-identify the data. Protected health information that may be removed and added back may include, for example, name, phone number, facsimile number, email address, social security number, medical record number, health plan beneficiary number, account number, certificate or license number, vehicle number, device number, URL, all geographical subdivisions smaller than a State, including street address, city, county, precinct, zip code, and their equivalent geocodes (except for the initial three digits of a zip code, if according to the current publicly available data from the Bureau of the Census), Internet Protocol number, biometric data, and any other unique identifying number, characteristic, or code.

The computer system 120 of the clinical event outcome scoring system 100 and method includes an adjustment module 217 comprising artificial intelligence utilizing adaptive self-learning capabilities using machine learning technologies. The capacity for self-reconfiguration enables the system 100 and method to be sufficiently flexible and adaptable to detect and incorporate trends or differences in the underlying patient data or population that may affect the predictive accuracy of a given statistical model. The adjustment module 217 may automatically modify or improve a statistical model in a number of exemplary ways. The adjustment module may evaluate new variables present in the data feed but not used in the statistical model, which may result in improved accuracy. For example, given that the patient attribute data set will be based on a set number of patient attributes, in one embodiment, the system may be configured to be able to take into account when calculating a SICK score. additional patient attributes for patients considered to be "outlier patients" (with additional significant patient attributes that are considered to affect the patient outcome). Likewise, in one embodiment, the system may be configured to be able to take into account additional patient outcomes for patients considered to be outlier patients. The adjustment module 217 may periodically retrain a selected statistical model for improved accurate outcome to allow for selection of the most accurate statistical methodology, number of patient attributes in the data set, the selection of patient attributes, weights, etc. The adjustment module 217 may compare the actual observed outcome of the clinical event to the predicted outcome then separately analyze the patient attributes within the model that contributed to the incorrect outcome. It may then re-weigh the patient attributes that contributed to this incorrect outcome, so that in the next reiteration those variables are less likely to contribute to a false prediction. In this manner, the system is adapted to reconfigure or adjust the statistical model based on the specific clinical setting or population in which it is applied. In one embodiment, the system is configured to generate one statistical model for a specific clinical event outcome (the "genus" statistical model) and then "species" statistical models related thereto, focused on the specific clinical setting or population in which it is applied. The adjustment module 217 may also be useful to scale the statistical model to different health systems, populations, and geographical areas in a rapid timeframe.

In one embodiment, the clinical event outcome scoring system 100 and method comprises: a data store configured to receive and store training data associated with a plurality of patients including clinical and non-clinical training patient attribute data and outcome data relevant to a clinical event; at least one statistical model including a plurality of weighted, categorized risk patient attributes and categorized clinical event outcomes to calculate a SICK score for a patient about to undergo a related clinical event; an assessment module configured to apply the at least one statistical model to patient clinical and non-clinical patient attribute data of a patient to determine at least one SICK score associated with the at least one specified clinical event for each patient, and a data presentation module configured to present the SICK score. In one embodiment, the clinical event outcome scoring system 100, comprises: a data store configured to receive and store data associated with a plurality of patients including clinical and non-clinical training patient attribute data and outcome data relevant to a clinical event; at least one statistical model including a plurality of weighted, categorized risk patient attributes and categorized clinical event outcomes to calculate a SICK score for a patient about to undergo a related clinical event; an assessment module configured to apply the at least one statistical model to patient clinical and non-clinical patient attribute data of a patient to determine at least one SICK score associated with the at least one specified clinical event for each patient, a data presentation module configured to present the SICK score, and an adjustment module configured to adjust parameters in the statistical model in response to trends in the patient data. In one embodiment, the clinical event outcome scoring system 100 and method and method for providing a SICK score comprises: receiving and storing data associated with a plurality of patients including clinical and non-clinical training patient attribute data and outcome data relevant to a clinical event; processing the clinical and non-clinical training patient attribute data and outcome data to generate at least one statistical model including a plurality of weighted, categorized risk patient attributes and categorized clinical event outcomes; using the statistical model to calculate a SICK score for a patient about to undergo a related clinical event; presenting at least one of visual and audible notification to a health care team, and monitoring and adjusting parameters in the statistical model in response to trends in the patient clinical and non-clinical data.

Each of the client devices may interact with the clinical event outcome scoring system 100 and method to transmit the patient attribute data for a patient about to undergo a clinical event. In some embodiments, patient attribute data may be collected periodically (e.g., every month, every three months, every six months, etc.) to identify changes to the patient's SICK score over time (e.g., from unemployed to employed, single to married, etc.). Also, in some embodiments, at least some of the patient attribute data may be recorded by a health care provider via the health care provider's client device or may be self-reported via the patient's client device.

Figure 4:
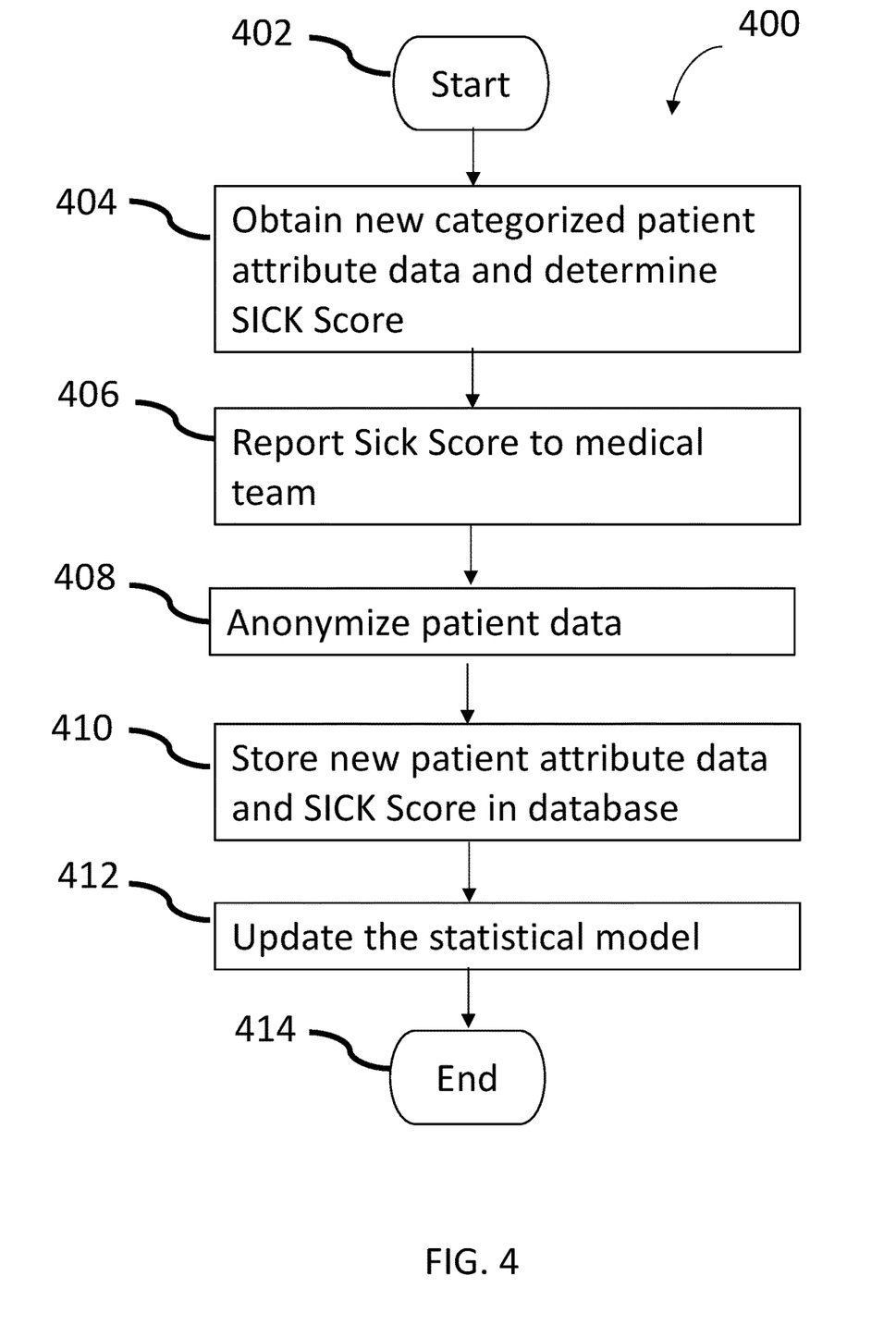
FIG. 4 is a simplified flowchart/block diagram of an exemplary embodiment of a clinical predictive and monitoring method according to the present disclosure.

In any event, the machine learning engine may receive electronic data from the client devices. For example, the machine learning engine may obtain a set of training data by receiving physiological and lifestyle patient attribute data. Additionally, the machine learning engine may obtain a set of training data by receiving physiologic and lifestyle patient attribute data from the training patients, such as the outcomes observed for a cohort of patients having undergone the same clinical event.

In a testing phase, the training module may compare test patient attribute data for a test patient to the statistical model to determine a likelihood of a specific adverse outcome event.

If the training module makes the correct determination more frequently than a predetermined threshold amount, the statistical model may be adjusted to reflect a tighter correlation. On the other hand, if the training module does not make the correct determination more frequently than the predetermined threshold amount, the training module may continue to obtain training data for further training.

Incorporating Quantum Computing Processor into the System

One skilled in the art of quantum computing would appreciate and understand how classical computers and quantum computers could be combined to explore multiple answers to come up with complex decisions. Quantum computers allow for multiple calculations to be performed simultaneously. In contrast to a "bit" in classical computing, which can take on a value of zero or one, quantum bits or "qubits" in quantum computing can scale exponentially, so that a two-qubit machine allows for four calculations simultaneously, a three-qubit machine allows for eight calculations, and a four-qubit machine performs 16 simultaneous calculations.

In one embodiment, the "what if" scenarios are performed on a supercomputer, or using a quantum computer, or using a quantum processor.

A quantum processor may take the form of a superconducting quantum processor. A superconducting quantum processor may include a number of qubits and associated local bias devices. A superconducting quantum processor may also employ couplers to provide tunable communicative connections between qubits. A qubit often will have more devices associated with it. In some embodiments, the methods and processes described herein may be tied to a quantum computing system of one or more quantum computing devices. One skilled in the art would understand the various aspects of an example quantum computer configured to execute quantum-logic operations (vide infra). Whereas conventional computer memory holds digital data in an array of bits and enacts bit-wise logical operations, a quantum computer holds data in an array of qubits and operates quantum-mechanically on the qubits in order to implement the desired logic. Accordingly, a quantum computer includes at least one register comprising an array of qubits. For example, the register is eight qubits in length; registers comprising longer and shorter qubit arrays are also envisaged, as are quantum computers comprising two or more registers of any length.

The qubits of the register may take various forms, depending on the desired architecture of quantum computer. Each qubit may comprise: a superconducting Josephson junction, a trapped ion, a trapped atom coupled to a high-finesse cavity, an atom or molecule confined within a fullerene, an ion or neutral dopant atom confined within a host lattice, a quantum dot exhibiting discrete spatial- or spin-electronic states, electron holes in semiconductor junctions entrained via an electrostatic trap, a coupled quantum-wire pair, an atomic nucleus addressable by magnetic resonance, a free electron in helium, a molecular magnet, or a metal-like carbon nanosphere, as nonlimiting examples. More generally, each qubit may comprise any particle or system of particles that can exist in two or more discrete quantum states that can be measured and manipulated experimentally. For instance, a qubit may also be implemented in the plural processing states corresponding to different modes of light propagation through linear optical elements (e.g., mirrors, beam splitters and phase shifters), as well as in states accumulated within a Bose-Einstein condensate.

A quantum computer includes a controller. The controller may comprise conventional electronic componentry, including at least one processor and associated storage machine. The term 'conventional' is applied herein to any component that can be modeled as an ensemble of particles without considering the quantum state of any individual particle. Conventional electronic components include integrated, microlithographed transistors, resistors, and capacitors, for example. Storage machine may be configured to hold program instructions that cause processor to execute any process described herein. Additional aspects of controller are described hereinafter.

The Controller of a quantum computer s configured to receive a plurality of inputs and to provide a plurality of outputs. The inputs and outputs may each comprise digital and/or analog lines. At least some of the inputs and outputs may be data lines through which data is provided to and extracted from the quantum computer. Other inputs may comprise control lines via which the operation of the quantum computer may be adjusted or otherwise controlled.

The Controller is operatively coupled to the register via an interface. The interface is configured to exchange data billirectionally with the controller. The interface is further configured to exchange signal corresponding to the data billirectionally with the register. Depending on the architecture of the quantum computer, such signal may include electrical, magnetic, and/or optical signal. Via signal conveyed through the interface, the controller may interrogate and otherwise influence the quantum state held in the register, as defined by the collective quantum state of the array of qubits. To this end, the interface includes at least one modulator and at least one demodulator, each coupled operatively to one or more qubits of the register. Each modulator is configured to output a signal to the register based on modulation data received from the controller. Each demodulator is configured to sense a signal from the register and to output data to the controller based on the signal. The data received from the demodulator may, in some scenarios, be an estimate of an observable to the measurement of the quantum state held in the register.

More specifically, a suitably configured signal from modulator may interact physically with one or more qubits of the register to trigger measurement of the quantum state held in one or more qubits. The Demodulator may then sense a resulting signal released by the one or more qubits pursuant to the measurement, and may furnish the data corresponding to the resulting signal to the controller. Stated another way, the demodulator may be configured to reveal, based on the signal received, an estimate of an observables reflecting the quantum state of one or more qubits of the register, and to furnish the estimate to controller. In one non-limiting example, the modulator may provide, based on data from the controller, an appropriate voltage pulse or pulse train to an electrode of one or more qubits, to initiate a measurement. In short order, the demodulator may sense photon emission from the one or more qubits and may assert a corresponding digital voltage level on an interface line into the controller. Generally speaking, any measurement of a quantum-mechanical state is defined by the operator O corresponding to the observable to be measured; the result R of the measurement is guaranteed to be one of the allowed eigenvalues of O. In quantum computer, R is statistically related to the register state prior to the measurement, but is not uniquely determined by the register state.

Pursuant to appropriate input from the controller, the interface may be further configured to implement one or more quantum-logic gates to operate on the quantum state held in register. Whereas the function of each type of logic gate of a conventional computer system is described according to a corresponding truth table, the function of each type of quantum gate is described by a corresponding operator matrix. The operator matrix operates on (i.e., multiplies) the complex vector representing the register state and effects a specified rotation of that vector in Hilbert space.

Suitably configured signal from modulators of the interface may interact physically with one or more qubits of the register so as to assert any desired quantum-gate operation. As noted above, the desired quantum-gate operations are specifically defined rotations of a complex vector representing the register state. In order to effect a desired rotation, one or more modulators of the interfaces may apply a predetermined signal level Si for a predetermined duration T i.

In some examples, plural signal levels may be applied for plural sequences or otherwise associated durations. In a more particular example, the plural signal levels and durations are arranged to form a composite signal waveform, which may be applied to one or more qubits of the register. In general, each signal level Si and each duration Ti is a control parameter adjustable by appropriate programming of controller. In other quantum-computing architectures, different sets of adjustable control parameters may control the quantum operation applied to the register state.

EXAMPLES

Example 1: One embodiment of the clinical event outcome scoring system as applied to Bariatric Surgical Patients, wherein the patient attributes have been processed by the system to generate categories of disease, rather than using direct clinical data, and also demonstrating a 1-4 classification scheme for patient attributes.

Examples of Some Common Patient Attributes.

| IDENTITY | LEVEL | ATTRIBUTE LEVEL CRITERIA | WEIGHTING FACTOR |
| --- | --- | --- | --- |
| Diabetes | 1 | Blood sugar between 90 and 140<br>Hgb A1C of 6-7<br>Taking an oral agent | a |
| Diabetes | 2 | Blood sugar between 140 and 180<br>HgbA1C of 7-8<br>Taking insulin plus one drug | a |
| Diabetes | 3 | Blood sugar between 180 and 220<br>HgbA1c of 8-9<br>Taking insulin plus more than one drug | a |
| Diabetes | 4 | Blood sugar above 220<br>HgbA1C of 9 of greater<br>Taking insulin plus more than one drug | a |
| Hypertension | 1 | Blood pressure 135/75-140/85<br>controlled by diet | b |
| Hypertension | 2 | Blood pressure 140/85-150 /90<br>Controlled by one or two medications | b |
| Hypertension | 3 | Blood pressure 150/90-165/ 95<br>Controlled by more than two medications | b |

-continued

| IDENTITY | LEVEL | ATTRIBUTE LEVEL CRITERIA | WEIGHTING FACTOR |
|---|---|---|---|
| Hypertension | 4 | Blood pressure 166/96-190/100 or above<br>Poorly controlled on three or more medications | b |
| Dyslipidemia | 1 | Controlled by diet<br>HDL-normal | c |
| Dyslipidemia | 2 | High LDL<br>Taking one medication | c |
| Dyslipidemia | 3 | High LDL<br>Taking two medications | c |
| Dyslipidemia | 4 | High triglyceride, low HDL and High LDL<br>Taking three medications. | c |
| Obstructive Sleep Apnea | 1 | Mild<br>No C PAP required | d |
| Obstructive Sleep Apnea | 2 | Requires C PAP | d |
| Obstructive Sleep Apnea | 3 | With Hypoventilation Syndrome | d |
| Obstructive Sleep Apnea | 4 | With $CO_2$ narcosis | d |
| Chronic Kidney Disease | 1 | Serum Creatinine level 1.2-1.8 | e |
| Chronic Kidney Disease | 2 | Serum Creatinine level 1.8-2.5 (or some number for the creatinine clearance)? | e |
| Chronic Kidney Disease | 3 | Serum Creatinine level 2.5-6.0 | e |
| Chronic Kidney Disease | 4 | Serum Creatinine > 6.0 and on dialysis | e |
| Coronary artery disease | 1 | Mild CHF, ejection fraction 50 | f |
| Coronary artery disease | 2 | Moderate CHF ejection fraction 30-40 | f |
| Coronary artery disease | 3 | Severe CHF ejection fraction 15-30 | f |
| Coronary artery disease | 4 | Very severe CHF ejection fraction < 15 | f |
| Emergency Dept visits in 2 years | 1 | 1-2 visits | g |
| Emergency Dept visits in 2 years | 2 | 3-5 visits | g |
| Emergency Dept visits in 2 years | 3 | 6-15 visits | g |
| Emergency Dept visits in 2 years | 4 | 16 or greater visits | g |
| Liver disease | 1 | normal liver function | h |
| Liver disease | 2 | normal liver function, but Hepatitis A,B | h |
| Liver disease | 3 | Hepatitis C | h |
| Liver disease | 4 | cirrhosis | h |
| Previous major surgery | 1 | zero | i |
| Previous major surgery | 2 | 1-3 | i |
| Previous major surgery | 3 | 4-6 | i |
| Previous major surgery | 4 | >6 | i |
| Mobility | 1 | Able to walk unassisted | j |
| Mobility | 2 | Able to walk with an assistance device, i.e., Cain, walker, crutches, etc. | j |
| Mobility | 3 | Needs assistance with ambulation at all times | j |
| Mobility | 4 | Bed bound | j |
| BMI | 1 | BMI 18-25 | k |
| BMI | 2 | BMI 26-30 | k |
| BMI | 3 | BMI 31-40 | k |
| BMI | 4 | BMI > 40 | k |
| Smoking status (tobacco) | 1 | Never smoked | l |
| Smoking status | 2 | Smoked < 5 years and quit | l |
| Smoking status | 3 | Smoking currently < than 5 years | l |
| Smoking status | 4 | Smoking currently for more than 5 years | l |
| Age-Adult | 1 | 18-25 | m |
| Age-Adult | 2 | 26-40 | m |
| Age-Adult | 3 | 41-65 | m |
| Age-Adult | 4 | >65 | m |

-continued

| IDENTITY | LEVEL | ATTRIBUTE LEVEL CRITERIA | WEIGHTING FACTOR |
|---|---|---|---|
| Education level | 1 | College or greater | n |
| Education level | 2 | finished high school or greater | n |
| Education level | 3 | did not finish high school | n |
| Education level | 4 | unable to read or write | n |
| Race | 1 | Caucasian | 0 |
| Race | 2 | Asian | 0 |
| Race | 3 | Hispanic | 0 |
| Race | 4 | Black | 0 |
| geographic residence location | 1 | Suburban residence | p |
| geographic residence location | 2 | Rural area residence | p |
| geographic residence location | 3 | Urban city limits | p |
| geographic residence location | 4 | Urban inner city | p |
| Alcohol usage | 1 | none | q |
| Alcohol usage | 2 | 1-5 drinks per week | q |
| Alcohol usage | 3 | 6-15 drinks per week | q |
| Alcohol usage | 4 | more than 15 drinks per week | q |

Other examples of patient attributes that can be used with this system and its related methods:
  Frailty Index
  Income
  Lung disease. (based upon their FEV-1 or other parameters)
  Some health status parameter
  Family history of illnesses
  Malignancy
  Narcotic usage (pain management)
  Peripheral vascular disease
  Tobacco usage
  Cognitive functional level (optionally can use existing scales)
  For surgical patients, their Anesthesia Score (ASA).

The invention claimed is:

1. A computer-implemented clinical event outcome scoring system, comprising:
  a data store comprising program instructions saved to memory and executable on a processor, said program instructions configured to receive and store historical data associated with a plurality of patients including clinical and non-clinical training patient attribute data and outcome data relevant to a clinical event, said patient attribute data comprising physiological attributes, lifestyle attributes, genetic attributes, belief attributes behavioral attributes, and psychological attributes, wherein a five-grade scale is used to indicate the degree of a patient attribute where zero indicates an absence of the attribute, one indicates a minimal measurable attribute, five indicates a highest extreme of an attribute, a three is midway point between one and five, a two is a midway point between one and three, and a four is a midway point between three and five;
  said physiological attributes comprising diabetes or hypertension, said lifestyle attributes comprising education level, socioeconomic, race, age, geographic residence location, income levels, family history of illness, tobacco usage, and exercise habits, said genetic attributes comprising genomics, epigenomics, chromatin state, transcriptomics, proteomics, and metabolomics, said belief attributes comprising possibility of recovery and patient foreseeing a desired outcome of a clinical event including thinner after bariatric surgery, recovery from a stroke, recovery from a myocardial infarction, being able to walk after a fractured hip repair, said behavioral attributes comprising disruptive behavior, bullying, argumentativeness, confrontationalness, said psychological attributes comprising depression, anxiety, bullying, confrontational state, obsessive compulsive, attention deficit disorder, addictive personality, and intellectual disability, and
  said clinical event selected from the group consisting of surgery, admission to hospital, radiation therapy, chemotherapy, home health care post discharge from the hospital, Emergency Department (ED) visit, physical therapy, and occupational therapy, said clinical event classified according to a national hospital survey statistic, and wherein a statistical model is generated for each type of clinical event, and wherein each type of clinical event has a historical profile of adverse events categorized into a complication level or grade, and
  wherein each said clinical event includes a grading scale used to indicate the severity or degree of a patient outcome from each clinical event, the grading scale calculated from a summation of weighted individual outcome indicia comprising recovery days in the hospital, visits to an emergency room, and serious complications, and,
  wherein a clinical event statistical model for a particular clinical event uses a grading scale to categorize the patient outcomes observed for a population of patients who have gone through the same clinical event, wherein a level 1-10 is assigned to categories of patient outcomes, including: Level 1: the ideal patient outcome for that clinical event: Level 2: increased hospital recovery time: Level 3: increased hospital recovery time+2 low grade (Grade I) complications: Level 4: increased hospital recovery time+>2 low grade (Grade I) complications+1 medium (Grade II) complication; Level 5: increased hospital recovery time+4 low grade (Grade I) complications+>2 medium (Grade II) complications; Level 6: increased hospital recovery time+>4 low grade (Grade I) complications+>4 medium (Grade II) complications+1 high (Grade III) complications; Level 7 worse than Level 6, Level 8 is the midpoint between Level 6 and 10, Level 9 is worse than 8, and Level 10: death within 30 days, wherein the training module generates a clinical event statistical model, that outputs a number ranging from 1-10;

a machine learning engine comprising program instructions saved to memory and executable on a processor, said program instructions configured to perform at least one statistical model including a plurality of weighted, categorized risk patient attributes and categorized clinical event outcomes to calculate a SICK score for a patient about to undergo a related clinical event, wherein one of said plurality of weighted, categorized risk patient attributes is a diabetes severity score calculated from patient clinical data comprising blood pressure, blood sugar level, HgbA1C level, HDL level, serum creatinine level, name and dosage of each medication, BMI, age, gender, wherein the statistician model is described by:

$$wf\alpha(att\ x) + wf\beta(att\ x) + wf\chi(att\ x) + wf\delta(att\ x) + wf\epsilon(att\ x) + etc. \ldots = outcome$$

where:

wf=weighting factor: values represented by $\alpha, \beta, \chi, \delta, \epsilon, \varphi, \gamma, \eta, \iota$, etc.

att=attribute (identity)+level (x), wherein x varies between 0-10 and wherein once outcome information has been converted into graded levels, the system back-calculates the weighting factors for each leveled patient attribute (wf=weighting factor: values represented by $\alpha, \beta, \chi, \delta, \epsilon, \varphi, \gamma, \eta, \iota$, etc.), by analyzing thousands of patient records for patients having undergone the same clinical event, to generate the clinical event statistical model;

a clinical event outcome scoring server comprising program instructions saved to memory and executable on a processor, said program instructions comprising an event outcome logic module configured to apply the at least one statistical model to clinical and non-clinical patient attribute data of at least one current patient to determine at least one SICK score associated with the at least one specified clinical event for such patient, and a data presentation module comprising program instructions saved to memory and executable on a processor, said program instructions configured to present the SICK score for each such patient; and an adjustment module having the capacity for self-reconfiguration that detects and incorporates trends or differences in the underlying patient data or population to adjust a predictive accuracy of a the statistical model, the adjustment module evaluating new variables for outlier patients present in the data feed but not used in the statistical model, and wherein the adjustment module configured to periodically retrain the statistical model by selecting a different statistical methodology, selecting the number of patient attributes in the data set, selecting patient attributes, selecting weights, and by comparing actual observed outcome of the clinical event to a predicted outcome and separately analyzing patient attributes within the statistical model that contributed to the incorrect outcome, and then re-weigh the patient attributes that contributed to this incorrect outcome, so that in the next reiteration those variables are less likely to contribute to a false prediction, wherein the statistical model reconfigured or adjusted based on a specific clinical setting or population in which it is applied.

2. The system of claim 1, wherein the machine learning engine and the clinical event outcome scoring server are configured to generate via the clinical event outcome scoring system a Pre-Clinical Event Care Plan for said patient detailing how to improve expected outcome by clinically modifying one or more of the attributes prior to the clinical event.

* * * * *